(12) United States Patent
Schmitt

(10) Patent No.: US 7,449,013 B2
(45) Date of Patent: Nov. 11, 2008

(54) DISPOSABLE ABSORBENT ARTICLE WITH WINGS PREDISPOSED TOWARDS THEIR IN-USE-POSITION

(75) Inventor: Achim Schmitt, Munster-Sarmsheim (DE)

(73) Assignee: The Procter & Gamble Company, Cincinnati, OH (US)

( * ) Notice: Subject to any disclaimer, the term of this patent is extended or adjusted under 35 U.S.C. 154(b) by 1826 days.

(21) Appl. No.: 09/242,014

(22) PCT Filed: Mar. 27, 1997

(86) PCT No.: PCT/US97/05008

§ 371 (c)(1),
(2), (4) Date: Apr. 5, 1999

(87) PCT Pub. No.: WO97/36563

PCT Pub. Date: Oct. 9, 1997

(65) Prior Publication Data

US 2002/0183707 A1 Dec. 5, 2002

(30) Foreign Application Priority Data

Mar. 30, 1996 (EP) .................................. 96105143

(51) Int. Cl.
*A61F 13/15* (2006.01)
(52) U.S. Cl. .............................. 604/385.04; 604/385.01
(58) Field of Classification Search ................. 604/378, 604/385.01, 385.03, 385.04, 386, 387, 389
See application file for complete search history.

(56) References Cited

U.S. PATENT DOCUMENTS

| 5,125,918 | A | * | 6/1992 | Seidy | 604/386 |
| 5,201,727 | A | * | 4/1993 | Nakanishi et al. | 604/390 |
| 5,217,448 | A | * | 6/1993 | Glaug et al. | 604/397 |
| 5,454,804 | A | * | 10/1995 | Widlund | 604/389 |
| 6,231,554 | B1 | * | 5/2001 | Menard | 604/385.01 |
| 6,231,556 | B1 | * | 5/2001 | Osborn, III | 604/385.1 |

* cited by examiner

*Primary Examiner*—Tatyana Zalukaeva
*Assistant Examiner*—Lynne Anderson
(74) *Attorney, Agent, or Firm*—David M. Wierich; Kevin C. Johnson

(57) ABSTRACT

The present invention relates to disposable absorbent articles such as sanitary napkins, panitiliners and incontinence pads that have side wrapping elements, also called wings on each longitudinal side edge of the article for protection of the side edges of the wearer's undergarment. The side wrapping elements are joined to the absorbent article such that they are predisposed towards their inuseposition, with the outermost edge of the side wrapping elements towards the longitudinal center line of the article. In this configuration the side wrapping elements can be unfolded by pulling the outermost edge of each side wrapping element in a transverse direction and applying the unfolded article to the crotch position of the wearers undergarment. The predisposition of the side wrapping elements will then support their folding around the undergarment side edges or even perform this task automatically.

1 Claim, 2 Drawing Sheets

DISPOSABLE ABSORBENT ARTICLE WITH WINGS PREDISPOSED TOWARDS THEIR IN-USE-POSITION

FIELD OF THE INVENTION

The present invention relates to disposable absorbent articles such as sanitary napkins, pantiliners and incontinence pads that have side wrapping elements, also called wings on each longitudinal side edge of the article for protection of the side edges of the wearer's undergarment. The side wrapping elements are joined to the absorbent article such that they are predisposed towards their in-use-position, with the outermost edge of the side wrapping elements towards the longitudinal centre line of the article. In this configuration the side wrapping elements can be unfolded by pulling the outermost edge of each side wrapping element in a transverse direction and applying the unfolded article to the crotch position of the wearers undergarment. The predisposition of the side wrapping elements will then support their folding around the undergarment side edges or even perform this task automatically.

BACKGROUND OF THE INVENTION

Absorbent articles such as sanitary napkins, pantiliners, and incontinence pads are devices that are typically worn in the crotch region of an undergarment. These devices are designed to absorb and retain liquid and other discharges from the human body and to prevent body and clothing soiling. Sanitary napkins are a type of absorbent article worn by women in a pair of panties which is normally positioned between the wearer's legs, adjacent to the perennial area of the body. Sanitary napkins in particular with side wrapping elements, often also referred to as side flaps or wings, are disclosed in the literature and are available in the marketplace.

Generally when sanitary napkins are provided with side flaps, the side flaps extend laterally from a central absorbent means and are intended to be folded around the edges of the wearer's panties in the crotch region. The side flaps can be provided with an attachment means for either affixing them to the underside of the wearer's panties or to the opposing side flap. The side flaps are particularly effective for preventing exudates from soiling the edges of the wearer's panties.

Sanitary napkins having wings or side flaps of various types are disclosed in U.S. Pat. No. 4,687,478, entitled "Shaped Sanitary Napkin With Flaps", U.S. Pat. No. 4,608,047, entitled "Sanitary Napkin Attachment Means", U.S. Pat. No. 4,589,876, entitled "Sanitary Napkin" and its Re-examination Pat. No. B1 4,589,876, U.S. Pat. No. 4,285,343, entitled "Sanitary Napkin". Sanitary napkins having wings are commonly viewed as providing good protection against soiling. Typically the side flaps are provided on the sanitary napkins by either being attached to the garment facing surface of the absorbent article or by integrally extending from the lateral side edges of the absorbent article.

Protective side flaps according to the prior art are provided such that their relaxed or predisposed position is assumed when the wings or flaps extend away from side edge of the main body portion of the absorbent article.

The side flaps are also typically folded inwards below or above the absorbent article for delivery such that a packaging can be provided to accommodate the basic width of the article without the side flaps. Tucked side flaps below the backsheet of the article which address this situation are known from PCT application PCT/US 9404926, PCT/US 9404927 and PCT/US 9404943. Alternative embodiments of tucked side wrapping elements are disclosed in European application 95114720.6.

In order to unfold the side flaps from this delivery position the user has to grab the edge of each side flap and unfold it into the basic flat position in order to place the absorbent article into the undergarment and fold the wings (against their predisposition) around the side edges of the crotch region of the undergarment.

EP-A-337438 discloses an attachment means for sanitary napkins by which resilient hinges are introduced to clamp the side edge of a wearers undergarments. This system suffers from the desire to resiliently attach the article to the crotch portion of the undergarment and hence requiring a hinge material which lacks comfort and can cause chaffing or skin irritation to the wearer.

The present invention addresses the problems of various available versions of side wrapping elements and improves their function in respect to soiling protection, convenience for the wearer, consistency of the crotch width of the article in use and maintains the comfort and non-irritation properties of the conventional side flaps.

Thus an objective of the present invention is to provide an absorbent article such as a sanitary napkin which is provided with an alternative to conventional side flaps by having a predisposition towards the in-use-position of the side flaps. It is another objective of the present invention to provide sanitary napkins with a defined crotch width after application to an undergarment independent of the various dimensions of undergarments and/or habits of wearers.

These and other objectives of the present invention will be more readily apparent when considered in reference with the following description and when taken in conjunction with the accompanying drawings.

SUMMARY OF THE INVENTION

The present invention relates to disposable absorbent articles for wearing in the crotch portion of an undergarment, in particular to sanitary napkins or pantiliners or adult continents inserts. The crotch portion of an undergarment comprises side edges which form part of the leg opening of the undergarment. The absorbent articles according to the present invention have a longitudinal and a transverse axis and comprise a main body portion which has longitudinal side edges substantially extending parallel to the longitudinal axis and transverse side edges substantially extending parallel to the transverse axis of the main body portion.

The main body portion further has a wearer facing surface which is oriented towards the wearer of such articles and a garment facing surface which is generally oriented towards the undergarment of the wearer.

The absorbent article according to the present invention comprises side wrappings elements which are wrapped around the side edges of the crotch portion of the undergarment. In this position the side wrapping elements have an in-use-position. According to the present invention the side wrapping elements have a predisposition so as to assume the in-use-position. This predisposition can be achieved by joining the side wrapping elements to the main body portion already in the in-use-position.

If the side wrapping elements are provided as separate pieces from the main body portion they are attached to the main body portion in their in-use-position, preferably to the garment facing surface and along the longitudinal side edges of the body portion of the disposable absorbent article.

In an alternative embodiment of the absorbent article the side wrapping elements are integral with the main body portion extending transversely away from the lateral axis of the absorbent article. The side wrapping elements are then folded along a foldline into the in-use-position and in order to provide the predisposition they are attached to the garment facing surface of the main body portion. It is preferred in this embodiment that the attachment is not longer than 50% of the length of the foldline of the side wrapping elements, preferably the midpoint of the line of attachment is in the vicinity of the midpoint of the foldline, for example within 10 mm from the midpoint of the foldline.

If the side wrapping elements are integral with the main absorbent body of the absorbent article they can be integral extensions of the topsheet which provides the wearer facing surface of the main body portion and/or integral extensions of the backsheet of the main body portion which provide the garment facing surface of the main body portion. In this embodiment it is preferred to have the side wrapping elements attached to the main body portion along the common portion of the longitudinal side edges of the main body portion and the side wrapping elements. The common portion of this attachment of the side wrapping elements to the main body portion can be preferably, at least partially between the foldline of the side wrapping elements into the in-use-position and the longitudinal axis of the absorbent article and thereby result in a non linear attachment line following the curvature of the main body portion. In such a case, if the attachment line is continuous, it is preferred that the material between the longitudinal side edges of the main body portion and the foldline where the side wrapping elements are folded into the in-use-position including the foldline itself is severed from the disposable absorbent article.

According to the present invention the attachment of the side wrapping elements to the main body portion of any of the embodiments can be provided by adhesive means or by welding of the contacting materials where the side wrapping elements touch the garment facing surface of the main body portion.

DETAILED DESCRIPTION OF THE INVENTION

Figure 1:
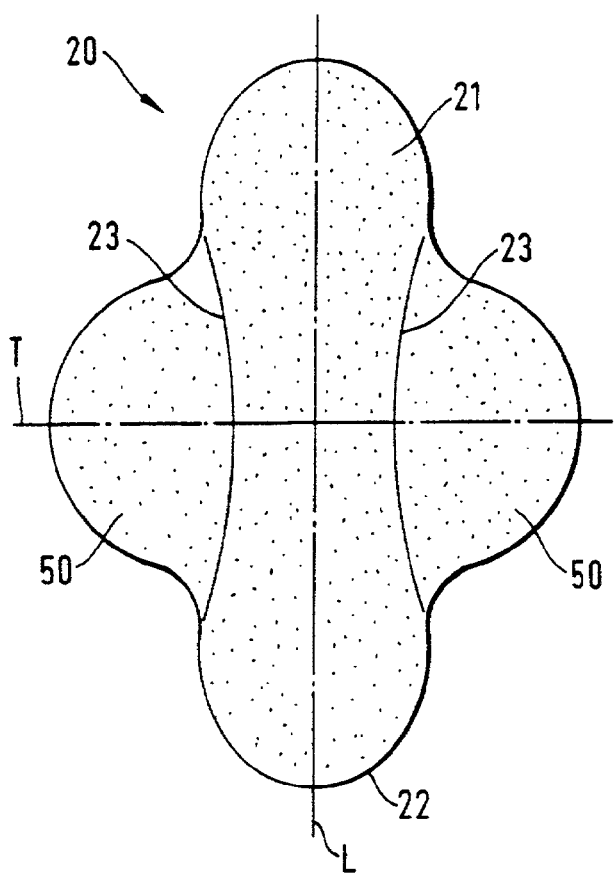
FIG. 1 is a top plan view of a conventional sanitary napkin having side wrapping elements.

FIG. 1 shows an embodiment of a disposable sanitary napkin 20 as known in the art. The present invention relates to absorbent articles, such as sanitary napkins, panty liners and incontinence pads and will be explained in the following by reference to sanitary napkins. According to the present invention sanitary napkins have a main body portion 21 and a pair of side wrapping elements 50 which wrap the side edges of the crotch portion of wearer's panties when the wearer places the sanitary napkin in the undergarments.

Figure 2:
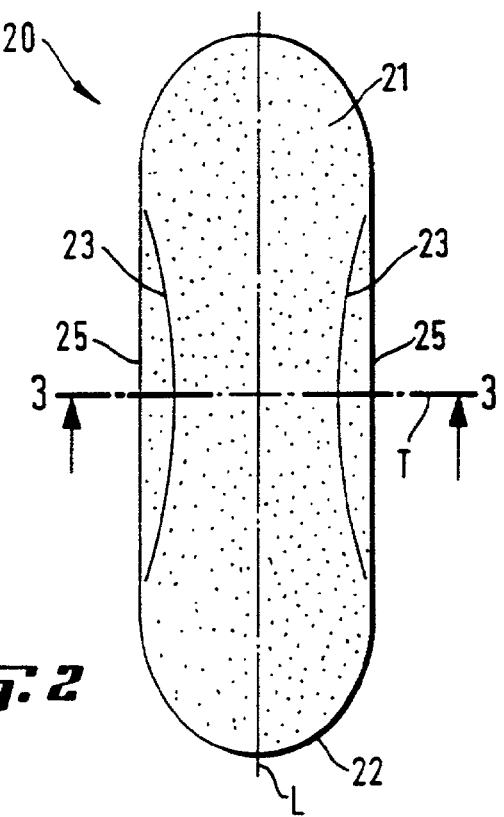
FIG. 2 is a top plan view of a sanitary napkin according to the present invention with the side wrapping elements predisposed into their in-use-position on the garment facing surface of the sanitary napkin.

The sanitary napkin 20 has two surfaces, a liquid pervious wearer facing surface and a preferably liquid impervious, garment facing surface. The sanitary napkin 20 is shown in FIGS. 1 and 2 as viewed from its wearer facing surface.

The sanitary napkin 20 has two axes, a longitudinal axis L and a transverse axis T. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" used herein, are interchangeable, and refer to a line, axis or direction which lies within the plane of the sanitary napkin 20 that is generally perpendicular to the longitudinal direction.

FIG. 1 shows the main body portion 21 of the sanitary napkin 20. The main body portion 21 comprises the portion of the sanitary napkin without the side wrapping elements 50. The main body portion 21 has two spaced apart longitudinal side edges 23, which can be linear or curved as shown in FIG. 1 or 2. A detailed description of a sanitary napkin and its main body portion is contained in U.S. Pat. No. 4,690,680.

The main body portion 21 of the sanitary napkin 20 can be of any thickness, including relatively thick, relatively thin, or even very thin. The sanitary napkin 20 shown is preferably a relatively thin sanitary napkin, preferably an "ultra-thin" sanitary napkin. An "ultra-thin" sanitary napkin 20 as described in U.S. Pat. Nos. 4,950,264 and 5,009,653 preferably has a calliper of less than about 3 millimeters.

Figure 3:
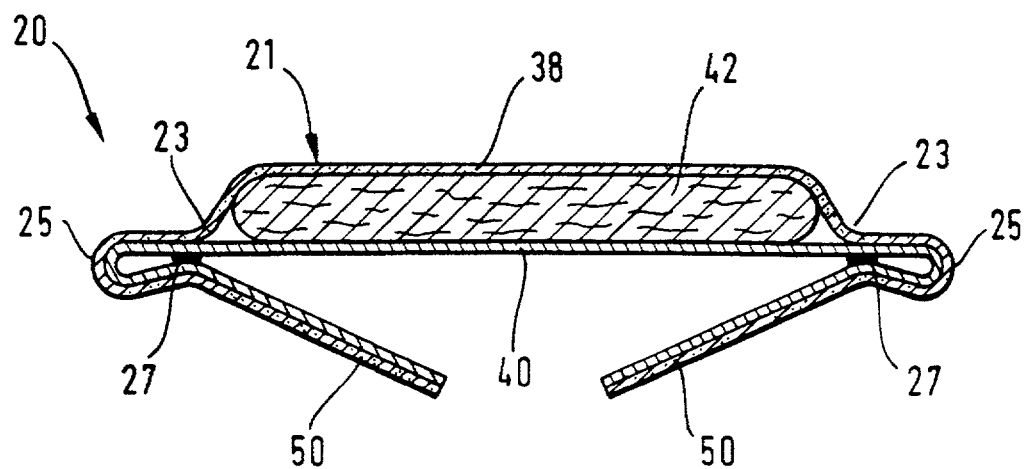
FIG. 3 is a cross sectional view along the transverse axis T of FIG. 2 showing an embodiment according the present invention.
Figure 4:
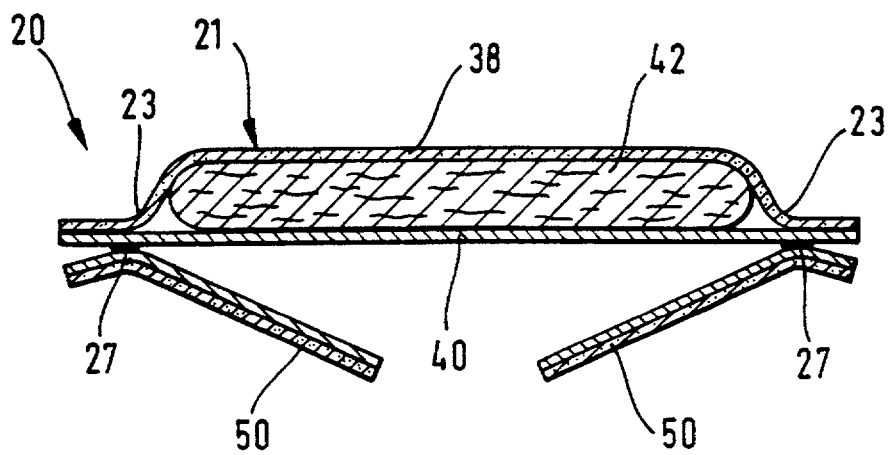
FIG. 4 is a cross sectional view of a preferred embodiment according the present invention which can be derived by further processing the embodiment as shown in FIG. 3.

FIG. 3 or 4 best show the individual components of the main body portion 21 of the sanitary napkin 20 of the present invention. The dimensions as shown in FIG. 3 or 4 should be considered as schematic only since some details are enlarged while other parts of the sanitary napkin may only be indicated or even not included in the Figures.

The main body portion 21 of the sanitary napkin generally comprises at least three primary components. These include a liquid pervious topsheet 38, a preferably liquid impervious backsheet 40, and an absorbent structure or core 42 positioned between the topsheet 38 and the backsheet 40. There are also occasions, however, when one or preferably more of these components, such as the backsheet and topsheet, can be replaced by a component that serves as part of the side wrapping elements 50 described below. The topsheet, the backsheet, and the absorbent core may be assembled in a variety of configurations known in the art (including so called "sandwich" products and "tube" products).

Several preferred sanitary napkin configurations are described generally in U.S. Pat. No. 4,321,924, "Bordered Disposable Absorbent Article"; U.S. Pat. No. 4,425,130, "Compound Sanitary Napkin"; U.S. Pat. No. 4,950,264, "Thin, Flexible Sanitary Napkin"; U.S. Pat. No. 5,308,346, "Elasticised Sanitary Napkin"; U.S. patent application Ser. No. 08/096,121 entitled "Absorbent Articles Having Panty Covering Components That Naturally Wrap the Sides of Panties" filed Jul. 22, 1993; and PCT Patent Application No. U.S. 94/10200 entitled "Absorbent Articles Having Panty Covering Components Comprising Extensible Web Materials Which Exhibit Elastic-Like Behaviour". The main body portion 21 of the sanitary napkin may also be comprised of one or more extensible components such as those sanitary napkins, and the like described in PCT Publication Nos. WO 93/01785 and 93/01786.

In general the three primary components of the main body portion need to satisfy the following:

The topsheet is compliant, soft feeling, and non-irritating to the wearer's skin. The topsheet also can have elastic characteristics allowing it to be stretched in one or two directions in portions of the topsheet or throughout its extension. Further, the topsheet is fluid pervious permitting fluids (e.g., menses and/or urine) to readily penetrate through its thickness. A suitable topsheet can be manufactured from a wide range of materials such as woven and non woven materials; polymeric materials such as apertured formed thermoplastic films, apertured plastic films, and hydroformed thermoplastic films; and thermoplastic scrims. Suitable woven and non woven materials can be comprised of natural fibers (e.g., wood or cotton fibers), synthetic fibers (e.g., polymeric fibers such as polyester, polypropylene, or polyethylene fibers) or from a combination of natural and synthetic fibers or bi-/multi-component fibers.

Preferred topsheets for use in the present invention are typically selected from high loft nonwoven topsheets and apertured formed film topsheets. Apertured formed films are especially preferred for the topsheets because they are pervious to body exudates and yet non absorbent and have a reduced tendency to allow fluids to pass back through and rewet the wearer's skin. Thus, the surface of the formed film that is in contact with the wearer remains dry, thereby reducing body soiling and creating a more comfortable feel for the wearer. Suitable formed films are described in U.S. Pat. Nos. 3,929,135; 4,324,246; 4,342,314; 463,045; and 5,006,394. Particularly preferred micro apertured formed film topsheets are disclosed in U.S. Pat. Nos. 4,609,518 and 4,629,643. A preferred topsheet for the present invention comprises the formed film described in one or more of the above patents and marketed on sanitary napkins by The Procter & Gamble Company of Cincinnati, Ohio as "DRI-WEAVE".

Topsheets having not a homogeneous distribution of liquid passage ways but only a portion of the topsheet comprising liquid passage ways are also contemplated by the present invention. Typically such topsheets would have the liquid passage ways oriented such that they result in a centrally permeable and peripherally impermeable topsheet for liquids.

The wearer facing surface of the formed film topsheet can be treated so as to help liquid to transfer though the topsheet. In a preferred embodiment, surfactant is incorporated into the polymeric materials of the formed film topsheet such as is described in PCT-publication WO 93/09741. Alternatively, the wearer facing surface of the topsheet can be made hydrophilic by treating it with a surfactant such as is described in U.S. Pat. No. 4,950,254. It has also been found that film topsheets can be treated to be hydrophobic which improves their dryness appearance.

Another alternative are so called hybrid topsheets which incorporate fibrous and film like structures particularly useful embodiments of such hybrid topsheets are disclosed in PCT publications WO 93/09744; WO 93/11725 or WO 93/11726.

The topsheet typically extends across the whole of the absorbent structure and outside the area coextensive with the absorbent structure. The topsheet can extend and form part or all of the preferred side flaps, side wrapping elements or wings as shown in FIG. 3.

When referring to the topsheet a multi layer structure or a mono layer structure is contemplated. The hybrid topsheet mentioned above is such a multi layer design but other multi layer topsheets such as primary and secondary topsheet designs are also considered.

The absorbent structure can include the following components: (a) optionally a primary fluid distribution layer preferably together with a secondary optional fluid distribution layer; (b) a fluid storage layer; (c) optionally a fibrous ("dusting") layer underlying the storage layer; and (d) other optional components.

a Primary/Secondary Fluid Distribution Layer

One optional component of the absorbent structure according to the present invention is a primary fluid distribution layer and a secondary fluid distribution layer. The primary distribution layer typically underlies the topsheet and is in fluid communication therewith. The topsheet transfers the acquired fluid to this primary distribution layer for ultimate distribution to the storage layer. This transfer of fluid through the primary distribution layer occurs not only in the thickness, but also along the length and width directions of the absorbent product. The also optional but preferred secondary distribution layer typically underlies the primary distribution layer and is in fluid communication therewith. The purpose of this secondary distribution layer is to readily acquire fluid from the primary distribution layer and transfer it rapidly to the underlying storage layer. This helps the fluid capacity of the underlying storage layer to be fully utilised. The fluid distribution layers can be comprised of any material typical for such distribution layers. In particular fibrous layers which can maintain the capillaries between fibers even when wet are useful as distribution layers.

b Fluid Storage Layer

Positioned in fluid communication with, and typically underlying the primary or secondary distribution layers, is a fluid storage layer. The fluid storage layer can comprise any usual absorbent material or combinations thereof. It preferably comprises absorbent gelling materials usually referred to as "hydrogel", "superabsorbent", hydrocolloid" materials in combination with suitable carriers.

The absorbent gelling materials are capable of absorbing large quantities of aqueous body fluids, and are further capable of retaining such absorbed fluids under moderate pressures. The absorbent gelling materials can be dispersed homogeneously or non-homogeneously in a suitable carrier. The suitable carriers, provided they are absorbent as such, can also be used alone.

Suitable absorbent gelling materials for use herein will most often comprise a substantially water-insoluble, slightly cross-linked, partially neutralised, polymeric gelling material. This material forms a hydrogel upon contact with water Such polymer materials can be prepared form polymerizable, unsaturated, acid-containing monomers which are well known in the art.

Suitable carriers include materials which are conventionally utilised in absorbent structures such as natural, modified or synthetic fibers, particularly modified or non-modified cellulose fibers, in the form of fluff and/or tissues. Suitable carriers can be used together with the absorbent gelling material, however, they can also be used alone or in combinations. Most preferred are tissue or tissue laminates in the context of sanitary napkins/panty liners.

An embodiment of the absorbent structure made according to the present invention comprises a double layer tissue laminate formed by folding the tissue onto itself. These layers can be joined to each other. Absorbent gelling material or other optional material can be comprised between the layers.

Modified cellulose fibers such as the stiffened cellulose fibers can also be used. Synthetic fibers can also be used and include those made of cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibers, tricomponent fibers, mixtures thereof and the like. Preferably, the fiber surfaces are hydrophilic or are treated to be hydrophilic. The storage layer can also include filler materials, such as Perlite, diatomaceous earth, Vermiculite, etc., to improve liquid retention.

If the absorbent gelling material is dispersed non-homogeneously in a carrier, the storage layer can nevertheless be locally homogenous, i.e. have a distribution gradient in one or several directions within the dimensions of the storage layer. Non-homogeneous distribution can also refer to laminates of carriers enclosing absorbent gelling materials partially or fully.

c Optional Fibrous ("Dusting") Layer

An optional component for inclusion in the absorbent structure according to the present invention is a fibrous layer adjacent to, and typically underlying the storage layer. This underlying fibrous layer is typically referred to as a "dusting" layer since it provides a substrate on which to deposit absorbent gelling material in the storage layer during manufacture of the absorbent structure. Indeed, in those instances where the absorbent gelling material is in the form of macro structures such as fibers, sheets or strips, this fibrous "dusting" layer need not be included. However, this "dusting" layer provides some additional fluid-handling capabilities such as rapid wicking of fluid along the length of the pad.

d Other Optional Components of the Absorbent Structure

The absorbent structure according to the present invention can include other optional components normally present in absorbent webs. For example, a reinforcing scrim can be positioned within the respective layers, or between the respective layers, of the absorbent structure. Such reinforcing scrims should be of such configuration as to not form interfacial barriers to fluid transfer. Given the structural integrity that usually occurs as a result of thermal bonding, reinforcing scrims are usually not required for thermally bonded absorbent structures.

Another component which can be included in the absorbent structure according to the invention and preferably is provided close to or as part off the primary or secondary fluid distribution layer are odor control agents. Active carbon and/or other odor control agents, in particular suitable zeolite and/or clay materials, are optionally incorporated in the absorbent structure. These components can be incorporated in any desired form but often are included as discrete particles.

The backsheet primarily prevents the exudates absorbed and contained in the absorbent structure from wetting articles that contact the absorbent product such as underpants, pants, pyjamas and undergarments. The backsheet is preferably impervious to liquids (e.g. menses and/or urine) and is preferably manufactured from a thin plastic film, although other flexible liquid impervious materials can also be used. As used herein, the term "flexible" refers to materials that are compliant and will readily conform to the general shape and contours of the human body. The backsheet also can have elastic characteristics allowing it to stretch in one or two directions.

The backsheet typically extends across the whole of the absorbent structure and can extend into and form part of or all of the preferred sideflaps, side wrapping elements or wings as shown in FIG. 3.

The backsheet can comprise a woven or non woven material, polymeric films such as thermoplastic films of polyethylene or polypropylene, or composite materials such as a film-coated non woven material. Preferably, the backsheet is a polyethylene film having a thickness of from about 0.012 mm (0.5 mil) to about 0.051 mm (2.0 mils).

Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The backsheet is preferably embossed and/or matte finished to provide a more clothlike appearance. Further, the backsheet can permit vapours to escape from the absorbent structure, i.e. be breathable, while still preventing exudates from passing through the backsheet. Also breathable backsheets comprising several layers, e.g. film plus non-woven structures or multilayerd films, can be used and are preferably joined to each other.

Side Flaps or Side Wrapping Elements

The side wrapping elements 50 can be of any suitable size and shape. The side wrapping elements 50 of the present invention may have any of the dimensions and characteristics set forth for the undergarment covering components in the aforementioned publications.

The side wrapping elements 50 can, as shown in FIG. 3, be integral with the main body portion 21. Alternatively the side wrapping elements 50 can, however, be joined to the main body portion 21 in any suitable manner.

The term "joined", as used herein, encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element.

The side wrapping elements 50 can be made from any of the materials used in the construction of the main body portion 21 of the sanitary napkin. The side wrapping elements 50 in the embodiment shown in FIG. 3 preferably comprise a laminate of two materials such as the topsheet and the backsheet material. Separately attached side wrapping elements can be made in the same fashion or from a different laminate, e.g. of a soft extensible coverstock material such as an extensible spunbond nonwoven web or a soft extensible formed film, an optional intermediate layer such as a three dimensional formed film, and a backing such as a polyethylene film backsheet material.

Suitable material for the side wrapping elements include those useful to provide the topsheet, the backsheet and optionally intermediate layers. In this context suitable nonwoven webs include a product known as Spunbond PE, which can be obtained from Polybond, Incorporated of Waynesboro, Va., USA and a product known as COROLIND PE, which can be obtained from Corovin GMBH of Germany.

As intermediate layer or as topsheet material a variation of a three dimensional formed film known as DRI-WEAVE can be used. DRI-WEAVE is used as a topsheet on sanitary napkins manufactured by the Procter & Gamble Company, Cincinnati, Ohio under U.S. Pat. Nos. 4,342,314 and 4,463,045. The three dimensional film for use in the side wrapping elements can be apertured or not apertured all the way through as in the case of DRI-WEAVE topsheet material. For integral side wrapping elements the DRI-WEAVE topsheet can be formed so that the apertures are closed off on the longitudinal side of the film which forms the wearer facing side of the side wrapping elements.

The polyethylene backsheet material can be for example a film as mentioned above. This polyethylene film can be joined to form the laminate of the side wrapping elements together with the nonwoven and/or the formed film by any suitable method such as by a spiral application of adhesives or slot coating, or it can be welded or extruded together.

The composite laminate preferably has a caliper of between 0.13-1.5 mm and is capable of extending between about 25-80% without tearing. The particular laminate is chosen to provide a soft body-contacting surface, good extensibility if extensibility is desired, good resistance to folding and crumpling and a liquid barrier.

The side wrapping elements 50 can be integral extensions of the topsheet 38 and backsheet 40 of the main body portion 21 as shown in FIG. 3. In other embodiments, instead of being integral, the side wrapping elements 50 can comprise a single or more separate components which are attached to the main body portion 21. They are preferably attached to the garment facing side of the main body portion 21 but can also be attached along the longitudinal side edge 23 of the main body portion 21 of the article 20.

According to the present invention the side wrapping elements 50 have a predisposition to as to assume the in-use-position. The in-use-position is similar to that shown in FIG. 3 or FIG. 4 in a cross sectional perspective where the crotch portion of the undergarment would be wrapped between the side wrapping elements 50 and the garment facing surface of the backsheet 40.

In order to achieve this predisposition it is not desirable according to the present invention to employ resilient hinges. In fact the use of an additional resilient hinge material in order to provide the side wrapping element 50 with the ability to clamp the napkin to the side edges of the crotch portion of the undergarment is undesirable according to the present invention since the additional resilient material can cause chaffing or it can be irritating to the sensitive skin on the inside of the thighs of their wearer.

If the side wrapping elements 50 are integral with the main body portion 21 of the sanitary napkin they can be formed by integral extensions as indicated above of the backsheet 40 and the topsheet 38 of the main body portion. Such a design is shown in a cross sectional view in FIG. 3.

The side wrapping elements 50 are then folded along a foldline 25 such that they depend from the main body portion on the side of the garment facing surface of the main body portion. The folding line 25 does not need to be a straight line but usually will be a straight line for geometry and material reasons and for simplicity of manufacturing.

This foldline 25 can be, but does not have to be, identical to the longitudinal side edges 23 of the main body portion 21 of the sanitary napkin 20. The main body portion 21 of the disposable absorbent article according the present invention can have and preferably has non-linear side edges. The main body portion essentially follows the peripheral outline of the absorbent structure and hence can for example assume a shape of a dog bone, hourglass, oval, have a different transversal dimension in the front and the rear end of the main body portion or it can be non-symmetrical in respect to the transverse axis.

Such a shape of the main body portion 21 is present in the prior art embodiment shown in FIG. 1. This prior art embodiment has integral side wrapping elements which are simply extensions of the components of the main body portion. The side wrapping elements are joined such that they are predisposed towards the flat, stretched out position shown in FIG. 1. This position can be considered as precursor of embodiments according to the present invention shown in FIG. 2, 3 or 4.

In case of a shaped main body portion 21 and a strait folding line 25 there will be a portion of the side wrapping element which is folded onto itself but remain outside the perimeter of the main body portion 21. Such a situation can be seen in the cross sectional view of FIG. 3. In principal this material can be considered excess material but need not be removed. However in a preferred embodiment according to the present invention this material, which is located between the folding line 25 and the longitudinal side edges 23 of the main body portion 21, is at least partially severed from the absorbent article 20 as can be seen in FIG. 4.

In order to provide the side wrapping element 50 with there predisposition towards the in-use-position it is provided with an attachment 27 to the garment facing surface of the main body portion. This attachment 27 can be provided by any means usual in the art such as by adhesive means by crimping, by soldering or by welding. Preferably this attachment 27 is extending along the longitudinal side edge 23 of the main body portion 21. However the attachment 27 can also be closer to or further away from the longitudinal axis than the longitudinal side edges 23 of the main body portion 21.

The attachment 27 need not be continues but can be provided in a discontinues fashion such as dots, dashes or points. In such a case it will be apparent to those skilled in the art that in order to maintain the primary function of side wrapping elements it is necessary to maintain a continues connection between the main body portion and the side wrapping elements to prevent soiling of the side edges of the crotch portion of the undergarment.

This can be achieved for integral side wrapping elements by maintaining the foldline 25 intact. For such an embodiment it is to preferred that the length of the line of attachment 27 does not exceed 50% of the length of the foldline 25, and even more preferable that the line of attachment 27 is substantially centred around the midpoint of the foldline, most preferably the line of attachment 27 has a midpoint within 10 mm of the midpoint of the foldline.

This embodiment is particularly useful for absorbent articles having strait longitudinal side edges along their main body portion. The side wrapping elements can then be predisposed towards their in-use-position such that the theoretical line, which is formed by connecting the transversely inner most points at which the side wrapping element is joint to the main body portion, such that this theoretical line forms an inwardly curved shape following more closely the usual curved shape of the side edges of the crotch portion of an undergarment than a strait line of attachment would.

In an alternative embodiment according to the present invention the side wrapping elements 50 can be provided as separate pieces from the main body portion 21. This has the benefit of allowing a different materials to be employed for the side wrapping elements than are use for the material forming the main body portion. The line of joining the separate side wrapping elements to the main body portion preferably can be identical to the line of attachment which provides the side wrapping elements with the predisposition towards their in-use-position. Such an embodiment would be identical to the cross sectional view of an embodiment according to the present invention having integral side wrapping elements of which the excess material including the folding line has been severed from the article as is shown in FIG. 4.

If the lines of attachment 27 of the side wrapping elements (50) to the main body portion are provided inward from the periphery of the main body portion, the free outwardly facing edge of the material forming the topsheet, the backsheet and the side wrapping elements can provide a particularly soft, non-irritating longitudinal side edge to the disposable absorbent article and is hence particularly preferred. To achieve this softness the free outwardly facing edge should have at least about 3 mm width along the longitudinal 30% of the longitudinal side edge of the main body portion.

Typically the side wrapping elements 50 comprise attachment means (not shown in the drawings) which can be any attachment means typically used in the art. This includes such attachments as the male part of mechanical fasteners, so called hooks, which engage into the fibrous surface of the undergarment as the complementary female loop part. More typical the attachment means is a pressure sensitive adhesive well known in the art which realisably adheres to the surface of the undergarment when placed in there. Suitable adhesives are Savare LA203 and LA303 of the Savare I.C. company of Milan in Italy, Coramelt 867 by Koemmerling in Pirmasens in Germany and Fuller H-2238ZP manufactured by the H.B. Fuller Co of Lueneburg in Germany. Suitable adhesive fasteners are also described in U.S. Pat. No. 4,917,697.

Prior to use the attachment means are protected by joining them to a release surface. The release surface has to be selected in accordance with the selection of the attachment means. For an adhesive attachment means a silicon coated release paper strip or more preferably a coating of the release compound onto the surface which is in contact with the attachment means in the article configuration as provided to the wearer can be employed.

ALTERNATIVE EMBODIMENTS

Numerous alternative embodiments of the present invention are possible. For example, the side wrapping elements are preferably mirror images of each other, and are symmetrical about the longitudinal axis. However, it should be understood that the shape and location of the side wrapping elements described herein are those of a preferred embodiment, and other embodiments are also possible. For example, while the side wrapping elements 50 are shown as extending symmetrical from each longitudinal edge of the main body portion, there may be one side wrapping element extending further than the other one. Further, the side wrapping elements 50 may be offset along the longitudinal centerline more towards one transverse end edge of the main body portion than the other.

The terms "panty liner" refer to absorbent articles that are less bulky than sanitary napkins which are generally worn by women between their menstrual periods. Suitable absorbent articles in the form of pantiliners that can benefit from the present invention described herein are disclosed in U.S. Pat. No. 4,738,676 entitled "Pantiliner".

The term "incontinence article" refers to pads, undergarments (pads held in place by a suspension system of same type, such as a belt, or the like), inserts for absorbent articles, capacity boosters for absorbent articles, briefs, bed pads, and the like, regardless of whether they are worn by adults, children or infants. Suitable incontinent articles that can be provided with the side wrapping elements described herein are disclosed in U.S. Pat. No. 5,300,054 and 5,304,161.

The invention claimed is:

1. Disposable absorbent article (20) for wear in an a undergarment, comprising: a longitudinal axis (L) and a transverse axis (T), said disposable absorbent article comprising a main body portion (21) having longitudinal side edges (23) substantially extending parallel to said longitudinal axis (L) and having transverse side edges (22) substantially extending parallel to said transverse axis (T), said main body portion (21) further having a wearer facing surface and a garment facing surface, and said disposable absorbent article composing side wrapping elements that are integral with said main body portion (21) said wrapping elements being folded along fold lines and attached to said garment facing side of said main body portion such that said side wrapping elements are pre-positioned in an in-use-position prior to the use of the disposable absorbent article.

* * * * *

UNITED STATES PATENT AND TRADEMARK OFFICE
CERTIFICATE OF CORRECTION

PATENT NO.         : 7,449,013 B2
APPLICATION NO. : 09/242014
DATED                 : November 11, 2008
INVENTOR(S)      : Achim Schmitt It is certified that error appears in the above-identified patent and that said Letters Patent is hereby corrected as shown below:

Title Page (*) Notice: Line 3, delete "1826" and insert -- 1955 --.

On Title Page Item [56] should read

U.S. Patent Documents

| | | |
|---|---|---|
| 4,589,876 | 5/86 | Van Tilburg |
| 4,687,478 | 8/87 | Van Tilburg |
| 5,354,400 | 10/94 | Lavash, et al. |
| 5,389,094 | 2/95 | Lavash, et al. |
| 5,620,430 | 4/97 | Bamber |
| 5,704,930 | 1/98 | Lavash, et al. |
| EP | 0 337 438 | 10/89 |
| EP | 0 530 781 | 3/93 |
| EP | 0 595 047 | 5/94 |
| EP | 0 695 542 | 8/94 |
| WO | WO 92/07537 | 5/92 |
| WO | WO 95/07675 | 3/95 |

(74) Attorney, delete "Wierich" and insert -- Weirich --.

(57) Abstract

Line 2, delete "panitiliners" and insert -- pantiliners --.

Line 7, delete "inuseposition," and insert -- in-use-position, --.

UNITED STATES PATENT AND TRADEMARK OFFICE
CERTIFICATE OF CORRECTION

PATENT NO.         : 7,449,013 B2
APPLICATION NO. : 09/242014
DATED                 : November 11, 2008
INVENTOR(S)        : Achim Schmitt It is certified that error appears in the above-identified patent and that said Letters Patent is hereby corrected as shown below:

Column 5

Line 25, delete "463,045;" and insert -- 4,463,045 --.

Claim 1

Line 9, delete "composing" and insert -- comprising --.

Signed and Sealed this

Fifteenth Day of September, 2009

David J. Kappos
*Director of the United States Patent and Trademark Office*

UNITED STATES PATENT AND TRADEMARK OFFICE
CERTIFICATE OF CORRECTION

PATENT NO. : 7,449,013 B2
APPLICATION NO. : 09/242014
DATED : November 11, 2008
INVENTOR(S) : Achim Schmitt It is certified that error appears in the above-identified patent and that said Letters Patent is hereby corrected as shown below:

Title Page (*) Notice: Line 3, delete "1826" and insert -- 1955 --.

On Title Page Item [56] should read

U.S. Patent Documents

| | | |
|---|---|---|
| 4,589,876 | 5/86 | Van Tilburg |
| 4,687,478 | 8/87 | Van Tilburg |
| 5,354,400 | 10/94 | Lavash, et al. |
| 5,389,094 | 2/95 | Lavash, et al. |
| 5,620,430 | 4/97 | Bamber |
| 5,704,930 | 1/98 | Lavash, et al. |
| EP 0 337 438 | 10/89 | |
| EP 0 530 781 | 3/93 | |
| EP 0 595 047 | 5/94 | |
| EP 0 695 542 | 8/94 | |
| WO WO 92/07537 | 5/92 | |
| WO WO 95/07675 | 3/95 | |

(74) Attorney, delete "Wierich" and insert -- Weirich --.

(57) Abstract

Line 2, delete "panitiliners" and insert -- pantiliners --.

Line 7, delete "inuseposition," and insert -- in-use-position, --.

UNITED STATES PATENT AND TRADEMARK OFFICE
CERTIFICATE OF CORRECTION

PATENT NO. : 7,449,013 B2
APPLICATION NO. : 09/242014
DATED : November 11, 2008
INVENTOR(S) : Achim Schmitt Page 2 of 2

It is certified that error appears in the above-identified patent and that said Letters Patent is hereby corrected as shown below:

<u>Column 5</u>

Line 25, delete "463,045;" and insert -- 4,463,045 --.

<u>Column 12, Claim 1</u>

Line 28, delete "composing" and insert -- comprising --.

This certificate supersedes the Certificate of Correction issued September 15, 2009.

Signed and Sealed this

Sixth Day of October, 2009

David J. Kappos
*Director of the United States Patent and Trademark Office*